United States Patent [19]

Blum

[11] 4,400,620
[45] * Aug. 23, 1983

[54] PHOTON EMISSION TOMOGRAPHIC APPARATUS

[76] Inventor: Alvin S. Blum, 2350 Del Mar Pl., Ft. Lauderdale, Fla. 33301

[*] Notice: The portion of the term of this patent subsequent to Jan. 11, 2000 has been disclaimed.

[21] Appl. No.: 312,653

[22] Filed: Oct. 19, 1981

Related U.S. Application Data

[63] Continuation-in-part of Ser. No. 163,057, Jun. 26, 1980, Pat. No. 4,368,389, and a continuation-in-part of Ser. No. 204,304, Nov. 5, 1980.

[51] Int. Cl.$^3$ .............................................. G01T 1/20
[52] U.S. Cl. ................................................ 250/363 S
[58] Field of Search ............... 250/360, 363 S, 445 T, 250/447, 451, 521, 522; 128/653, 654; 269/324, 325, 328, 908

[56] References Cited

U.S. PATENT DOCUMENTS

| | | | |
|---|---|---|---|
| 4,216,381 | 8/1980 | Lange | 250/363 S |
| 4,223,222 | 9/1980 | Gray et al. | 250/363 S |
| 4,229,656 | 10/1980 | Iversen et al. | 250/447 |

Primary Examiner—Alfred E. Smith
Assistant Examiner—Janice A. Howell

[57] ABSTRACT

Tomographic imaging system employs radiation detector rotated around radiation emitting patient. Body contour following action causes detector to approximate patient surface during rotation, thereby reducing detector/patient distance to improve image resolution. Another embodiment applies the same body contour following action to a system employing rotating patient support and fixed detector. Includes control of detector orientation relative to axis of rotation.

13 Claims, 3 Drawing Figures

PHOTON EMISSION TOMOGRAPHIC APPARATUS

This is a continuation in part of copending applications 6/163,057 filed 6/26/80, now U.S. Pat. No. 4,368,389, and 6/204,304 filed 11/05/80.

FIELD OF THE INVENTION

Apparatus and method for producing images of the distribution in three dimensions of photon emitting materials (radioactive pharmaceuticals) in the body including detector, detector support and body support.

DESCRIPTION OF THE PRIOR ART

Area radiation detectors of the scintillation camera type rotate around the subject containing radioactive material so as to view the radiation from a plurality of angles. Radiation detection information and detector position information are correlated by computer reconstruction to provide images of the distribution of the radioactive material within the body in a variety of views such as transverse or longitudinal slices through the body. Technicare Corp. has recently introduced a rotating counterbalanced detector whose radius of rotation can be adjusted before operation to a smaller cylinder to view the head or a child with shorter subject/detector distance.

However, the shape of the body and the cantilevered body support are not cylindrical, so that imaging the torso requires setting the radius to allow the detector to clear the support sides which means that when the detector is over the chest, it may be very far from the body surface, causing a loss of image resolution. Further, the geometry of the C arm detector support requires a cantilevered body support. The cantilevered body support requires great strength and rigidity of construction, interfering with design for adjustability to smaller bodies and thin construction for transparency to the radiation which must pass therethrough to the detector.

SUMMARY OF THE INVENTION

It is an object of the present invention to improve image quality by minimizing subject/detector distance. The present invention allows the radius of rotation to change during rotation to conform to the body contour, maintaining minimum subject/detector distance throughout the procedure. Improved patient support means allows adjustment to body size and reduces absorbing structure. Improved patient support design allows improved patient positioning, because body may now be supported at both ends without rotating detector support interference. Alternatively, patient support rotates before a fixed detector, while maintaining minimum patient detector distance.

The present invention privides a collimated, large area radiation imaging detector device including means for supporting said detector, means for moving said detector about a radiation emitting subject so as to view the subject from a plurality of angles. Means are provided to maintain close spacing between subject and detector during said movement to achieve optimum resolution of imaging of distribution of radiation emitting material within the subject including means for storing manually located detector positions in data processing means and automatically returning the detector to said positions during rotation and imaging. It is a further object of the present invention to provide patient support means including means for supporting one end of the patient support means by the rotating detector support means. It is a further object of the invention to provide spring loaded detector support means or slip clutch motor drive means to gently and yieldably press the detector against the body contours, body support means, body contour belt means and the like during its movement or rotation about the body. The body and detector act generally as cam and cam follower in this operation. Surfaces of a lubricous nature and guides on the leading edge of the detector may be provided to facilitate smooth movement therebetween. Counterweight means are provided at the opposite end of the detector support means to balance the mass of the detector so that as it moves in space, the only force of the face of the detector against the body, belt, or the like is a controlled spring motor force or slip clutch motor drive force. Support counterweight means may be further provided to balance the weight of the entire detector with its support means and counterweight means, thereby allowing the movement of the detector about the subject with relatively small and uniform force by support driving means. Improved body support means are provided allowing adjustment to body size and shape. Said body support means facilitate patient handling and positioning, reduce radiation absorbtion and enable closer patient/detector spacing.

Detector orientation indicator means and radius indicator means provide signals to data processor means. Data processor control means are provided to maintain the plane of the detector tangent to a cylinder of rotation and parallel to the axis of rotation during changes of radius of rotation. This is accomplished by storing in data processor memory the correct detector position data for every radius of rotation in advance and either manually or automatically orienting the detector to correct position corresponding to the particular radius.

Data processor means further provide information to computer image reconstruction means to shift image input data to the computer to correct for the translatory shift of the detector field of view which results from a change in the radius of rotation.

The parent application discloses means for single photon emission rotational tomography wherein a fixed radius of rotation is replaced by a variable radius of rotation. The disclosed variable radius of rotation includes body contour following means whereby the detector, as it rotates, is automatically approximated to the contours of the patient's body and/or the patient body support, whichever extends more outwardly toward the detector at that angle of rotation. Also included are means to maintain the orientation of the detector head so that the plane of the detector is tangential to the arc of rotation and parallel to the axis of rotation at all times even though the radius of rotation is changing. Also included are means to overcome the requirement of a thick cantilevered patient support.

Also included are means to correct the image displacement that radius of rotation changes induce with certain detector supports. It is an object of this disclosure to apply the invention to rotating C arm detector support systems.

Figure 1:
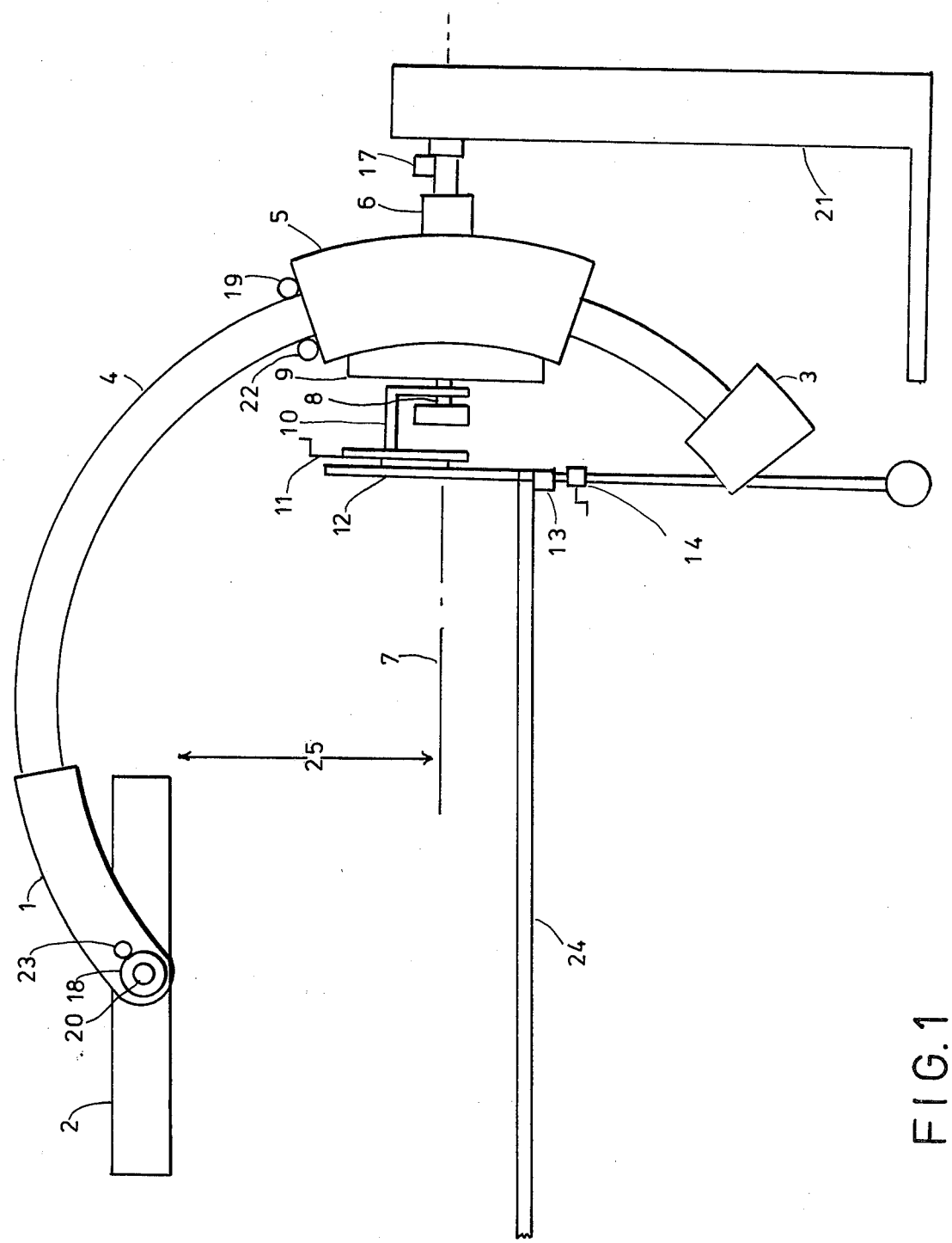
FIG. 1 is a front view of an embodiment of the invention wherein the detector is supported in a yoke at one end of a sliding, counterbalanced curved arm, including patient support.

FIG. 1 shows a side view of a preferred embodiment of the invention applied to a C arm detector support system. Stand 21 supports rotator 6 which rotates C arm track 5 about axis of rotation 7. C arm 4 carries yoke 1 with radiation detector 2 at one end, and counterweight 3 at its opposite end. C arm 4 slides in C arm track 5 either freely or driven by arc driver 22. Detector 2 is pivotally supported in yoke 1, rotating about pivot 20. Rotary position indicator means 18 indicates the tilt position of head 2 relative to yoke 1 and rotary position indicator 17 indicates the position of C arm 4 (and track 5) relative to stand 21. Arc position indicator 19 indicates position of C arm 4 and therefore detector 2 relative to C arm track 5, and radius of rotation 25.

In rotational tomography, regardless of whether radius is fixed or variable, it is desireable for the plane of the detector to be tangential to a cylinder of rotation and for the plane of the detector to be parallel to the axis of rotation at any point during the rotation when information is being acquired. For any particular position of C arm 4 in C arm track 5 (indicated by indicator 19), there will be only one tilt position of detector 2 in yoke 1 (indicated by indicator 18) that will provide this required tangential and parallel condition. The outputs of indicators 19 and 18 can be connected to data processing means containing calibration data such as a look up table of sets of readings of 19 and 18 which correspond to the required condition of tangent and parallel. A display may indicate the degree of closeness to the desired condition for manual adjustment of the degree of tilt of detector 2 for fixed radius tomography. Alternatively, motor drive means 23 may automatically adjust the tilt so that indicator 18 output is correct for the particular output of indicator 19. Arc driver 22 may automatically drive arc 4 in track 5 until detector 2 is pressed against patient. The driver 22 may be, e.g. a spring motor, or a motor with slip clutch so that force against patient is limited to a harmless level. As rotator 6 turns C arm 4, detector 2 will then automatically follow the body contour and automatically adjust to parallel the axis of rotation.

As detector 2 moves arcuately from a position close to the axis 7 to a position distant from the axis 7, its field of view moves translationally toward stand 21. This translational motion must be corrected for so that the computer can properly reconstruct the image. A function (cosine) of the output of arc position indicator 19 can be used to translationally shift the imaging data input to the computer. Alternatively, the patient or detector assembly may be moved by mechanical means the corresponding distance.

In another embodiment of the invention, the operator manually positions the detector to the contours of the patient (and support) while rotating about the axis. The automatic tilt adjustment will be helpful here. During this manual process, the data processor stores in memory the manually adjusted positions as signals from position indicators 17, 18 and 19. The system is then operated automatically while acquiring image data, and the drivers use the remembered positions to move the detector 22 around the patient and at the same time position the detector close to the patient by reproducing the manually located positions.

Patient Support/Bed

If the patient rests on a bed supported by legs at both ends, rotator 6 will not be able to rotate through 360 degrees because the set of legs near stand 21 will interfere with the motion of C arm 4. Current practice overcomes the limitation by employing a cantilevered bed supported at only one end. A disadvantage of this practice is that the support must be thick to hold the weight of the patient. Said thick support interferes with our object of decreasing detector/patient distance. A preferred embodiment shown in FIG. 1 provides body support 24 supported by bed end 16 and height adjustable legs 15 at a first end and by bed end 12 and height adjustable legs 14 at a second end. Legs 14 are removeably fastened to bed end 12 by connector 13. Bed holder 10 is connected to bed end 12 by vertical bed adjuster 11. Radial bearing 8 is rigidly connected to C arm track 5 by radial support 9 so that bearing 8 is coaxial with rotator 6 and strong enough to support one end of the bed.

For use, legs 14 and 15 are height adjusted so that body support 24 is coplanar with patient's stretcher/bed to facilitate sliding patient onto body support 24. With patient on support 24, bed holder 10 is adjusted with adjustor 11 so that axis of bearing 8 (and axis of rotation) will pass through patient at desired level. Legs 14 are raised so that holder 10 can clear bearing 8. Assembly is moved so that holder 10 is over bearing 8, then legs 14 are lowered until holder 10 fits over bearing 8 and it is locked in place by locking means not shown. Legs 14 are unlocked from connector 13 and lowered further and removed. Bed end 12 is now supported by the rotating assembly 5 but torque is not transmitted through radial bearing 8. C arm 4 is now free to sweep around patient without interference from legs 14. Legs 15 are adjusted so that axis of rotation will pass through patient at desired level. Support 24 may consist of various flexible planes or adjustable longitudinal slats that may convert from a planar surface suitable for patient transfer to an arcuate surface to further reduce detector/patient distance.

Figure 2:
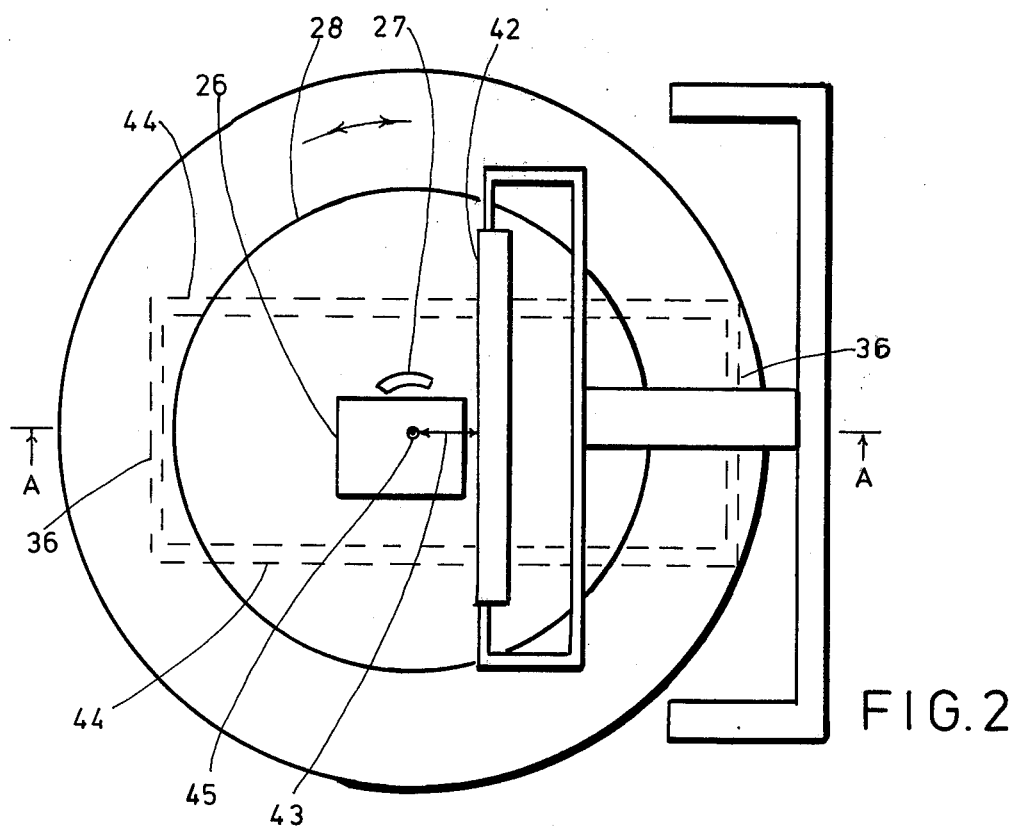
FIG. 2 is a plan view of a rotating patient support embodiment.
Figure 3:
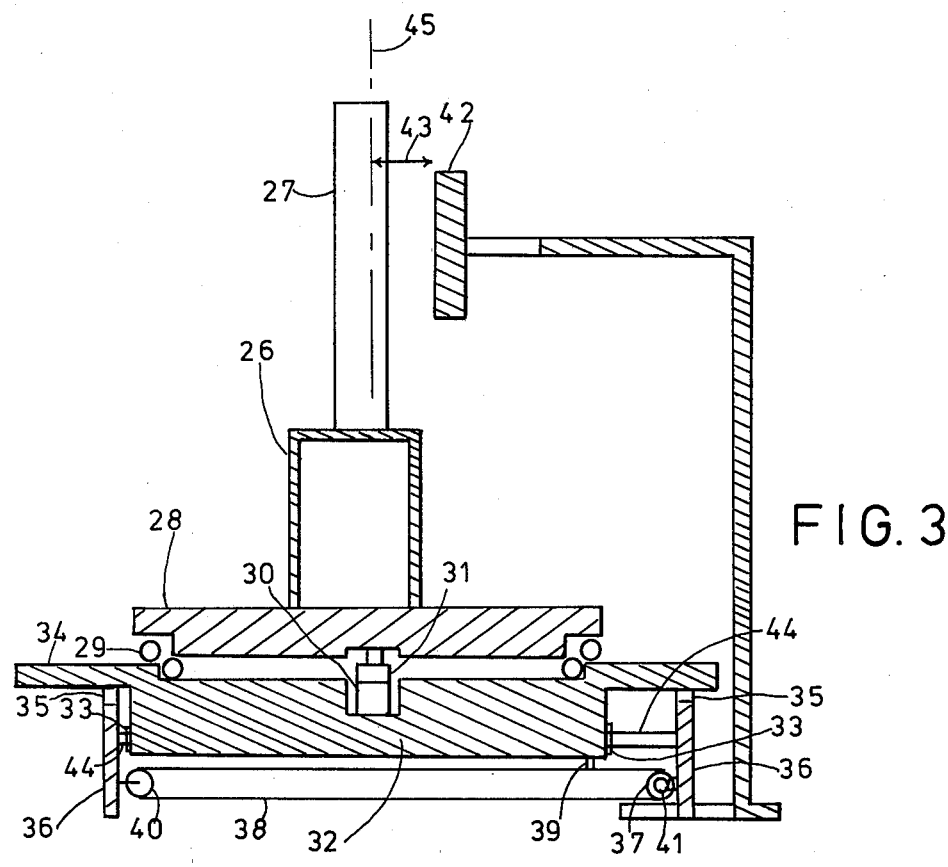
FIG. 3 is a cross section through line A—A of FIG. 2.

FIG. 2 shows a plan view of an embodiment of the invention wherein the detector is stationary and the patient is rotated, and FIG. 3 is a section through line A—A of FIG. 2. The patient sits in a chair 26 or astride a saddle if knee flexure obstructs positioning. He is immobilized with his back against vertical support 27. Rotator 30 rotates platform 28 and patient before detector 42. Platform 28 is supported in platform carrier 32 by radial thrust bearings 29 so that very little force is required to rotate patient. Rotator 30 may be a low power motor with slip clutch to prevent excess force being inadvertently applied to patient. Platform carrier 32 slides to and fro on a pair of support rods 44 fixed to stands 36. Ball bushings 33 reduce friction so that motion requires little force. Reversible drive motor 37 operates cable 38 around pulley 40 moving platform carrier 32 through connector 39 to provide to and fro motion to the platform to move patient toward or away from detector 42. Drive motor 37 may also be low power with slip clutch to prevent harm to patient. Skirt 34 protects support rods 44, and rollers 35 reduce friction against stand 36. Preliminary adjustment of the tilt of detector 42 will ensure that the plane of the detector is parallel to the axis of rotation 45 and tangential to the arc of rotation throughout the rotation. As platform 28 moves to and fro, the axis of rotation will advance and retreat from the detector and the radius of rotation 43 will decrease and increase, but there will be no translation of the field of view requiring computer correction.

Position indicator 31 provides a signal related to the degree of rotation of platform 28. Position indicator 41 provides a signal related to the radius of rotation 43. In a preferred mode of operation, with patient on platform, the operator rotates the platform while manually adjusting the radius of rotation 43 so as to maintain the minimum distance between patient and detector 42. During this manual process, the signals from position indicators 41 and 31 are stored in data processor memory as sets of values with a value for indicator 31 and a corresponding value for indicator 41 as set manually. The system is then operated in the automatic mode. As rotator 30 rotates the patient, position indicator 31 signals the data processor which finds the corresponding signal value for indicator 41 stored in memory during the manual operation. Drive motor 37 is actuated until the signal from indicator 41 reaches this stored value. By this process, the patient is automatically rotated before the detector during the radiation measuring phase and the radius of rotation is automatically adjusted to exactly follow the patient contour as determined during the manual adjustment. Patient support 26 may be movable relative to platform 28 so that axis of rotation may be positioned to pass through the center of an organ of interest.

What is claimed is:

1. A structure for a radiation detector for emission tomography imaging of a radioactive patient comprising: counterbalanced detector support means; rotation means for rotating said detector about an axis and around said patient so as to view said patient from a plurality of angles; radius adjusting means to adjust the radius of rotation of said detector during said rotation around said patient so as to maintain a minimum distance between said detector and said patient to improve image quality.

2. The invention of claim 1, wherein said detector support means includes arcuate member means and arcuate member holder means, and said radius adjusting means includes means moving said arcuate member means within said arcuate member holder means, said arcuate member holder means rotating about an axis.

3. The invention of claim 1, including horizontal patient support means, said patient support means being supported at at least one of its ends by rotary bearing means, said rotary bearing means being coaxial with the axis of rotation of said rotating detector, said rotary bearing means being connected to and supported by said detector support means so as to prevent interference with detector rotation, said rotary bearing means preventing transmission of torque forces to said patient support means.

4. The invention of claim 1, further comprising means for maintaining a plane of said detector means tangential to an arc of rotation of said detector means at all angles of rotation.

5. The invention of claim 4, including: detector orientation sensing means; radius of rotation sensing means; data processing means; and detector orienting means, said data processing means storing detector orientation sensing means data and radius of rotation sensing means data in combinations corresponding to conditions wherein said plane of said detector is tangential to an arc of rotation and parallel to the axis of rotation, said detector orienting means orienting said detector means until said data processor means indicates that detector orientation sensing means output and radius of rotation sensing means output match stored combination corresponding to a condition wherein a plane of said detector means is tangential to an arc of rotation and parallel to said axis of rotation at all angles of rotation.

6. The invention of claim 2, including detector position sensing means, said detector position sensing means communicating body contour following motions of said detector means to computer means to provide for appropriate correction for detector field of view displacement for computer image reconstruction.

7. The invention of claim 1, including: detector orientation and position sensing means; radius of rotation sensing means; angular rotation sensing means; data processor means; detector orienting and positioning means;

wherein said data processor means stores sensing data during preliminary rotation of said detector means about said patient while said radius of rotation is being manually adjusted for minimum patient/detector spacing, and subsequently said detector orienting and positioning means, said rotation means and said radius adjusting means automatically, under the control of said data processor means, using said stored sensing data and current sensing data, rotates said detector means around said patient while reproducing the detector positions of the preliminary manual operation.

8. The invention of claim 3, including bearing adjusting means for vertical adjustment of said rotary bearing means relative to said horizontal patient support means so that axis of rotation can be made to pass through selected region of the patient.

9. Body rotation tomography imaging system for radiation detector means, comprising: body support means; body support rotation means; body contour following means, said body contour following means including translatory motion means for moving said rotational body support means toward or away from said detector means, said body contour following means causing said body to be approximated to said detector means while said body is rotated before said detector means; rotation position sensing means; translation position sensing means; and data processor means, wherein said data processor means stores sensing data during preliminary rotation of said patient support means while manually adjusting translatory position for minimum patient/detector spacing, and subsequently said rotation means and said translatory motion means automatically, under the control of said data processor means, using current sensing data and stored sensing data, rotate the patient before said detector means while reproducing the positions of the preliminary manual operation.

10. The invention of claim 1, including: detector radius of rotation sensing means; data processing means; and image data storage means, said sensing means providing radius of rotation information to said data processing means, and said data processing means providing appropriate correction for displacement of detector field of view resulting from change of radius of rotation by corresponding displacing of image data to said image data storage means.

11. The invention of claim 1, including: detector radius of rotation sensing means; data processing means; and patient displacement means, said sensing means providing radius of rotation information to said data processing means, and said data processing means providing appropriate correction for detector field of view displacement resulting from change of radius of rotation by correspondingly displacing said patient by means of said patient displacement means connected to said data processing means.

12. The invention of claim 1, including: detector radius of rotation sensing means; data processing means; and detector displacement means, said sensing means providing radius of rotation information to said data processing means, and said data processing means providing appropriate correction for detector field of view displacement resulting from change of radius of rotation by correspondingly displacing said detector means by means of said detector displacement means connected to said data processing means.

13. A radiation imaging system with radiation detector means for tomographic analysis of a patient, comprising: detector support means; rotation means for rotating said detector means about an axis and around said patient so as to view said patient from a plurality of angles; radius adjusting means to adjust the radius of rotation of said detector means during said rotation to maintain a minimum distance between said detector and said patient for optimum image resolution; detector position information storage means; and detector position following means, said detector position information storage means storing detector position information generated during preliminary rotation of said detector means while manually adjusting said system for minimum detector/patient distance, and said detector following means automatically reproducing detector positions of the preliminary manual operation using said stored detector position information during a subsequent automatic detector rotation.

* * * * *